US00PP10504P # nited States Patent [19]

ıaal

[11] Patent Number: Plant 10,504

[45] Date of Patent: Jul. 14, 1998

| BEGONIA PLANT NAMED 'CAVILI'

| Inventor: Andre Smaal, Aalsmeer, Netherlands

| Assignee: Begonia Breeders Assoc. B.V., Aalsmeer, Netherlands

| Appl. No.: 811,739

| Filed: Mar. 6, 1997

| Int. Cl.[6] ..... A01H 5/00

| U.S. Cl. ..... Plt./87.18

| Field of Search ..... Plt./87.17, 87.18

*Primary Examiner*—James R. Feyrer

*Attorney, Agent, or Firm*—C. A. Whealy

[57] ABSTRACT

A distinct cultivar of Begonia plant named 'Cavili', characterized by its attractive pink fully double flowers that are about 6.5 cm in diameter; resistant to powdery mildew under commercial greenhouse conditions; and excellent postproduction longevity.

1 Drawing Sheet

1

'he present invention relates to a new and distinct cultivar 3egonia plant, botanically known as *Begonia×hiemalis*, ımercially known as Elatior Begonia, and referred to by cultivar name 'Cavili'.

'he new cultivar is a product of a planned breeding gram conducted by the inventor in Aalsmeer, The Nethnds. The objective of the breeding program is to create ' Begonia cultivars having good postproduction longevand resistance to powdery mildew.

'he new cultivar originated from a cross made by the :ntor in Aalsmeer, The Netherlands, of *Begonia tuberosa* ıe female, or seed, parent with *Begonia socotrana*; as the e, or pollen, parent.

'he cultivar 'Cavili' was discovered and selected by the :ntor as a flowering plant within the progeny of the stated :s in a controlled environment in Aalsmeer, The Nethnds. The selection of this plant was based on its desirable /er color, uniform plant habit, numerous flowers, good 'production longevity and mildew resistance.

ısexual reproduction of the new cultivar by terminal ings taken in a controlled environment in Aalsmeer, The herlands, has shown that the unique features of this new onia are stable and reproduced true to type in successive erations.

he cultivar 'Cavili' has not been observed under all ıible environmental conditions. The phenotype may vary ıewhat with variations in environment such as tempera-, daylength and light intensity, without, however, any ance in genotype.

he following traits have been repeatedly observed and determined to be the unique characteristics of 'Cavili'. se characteristics in combination distinguish 'Cavili' as :w and distinct cultivar:

. Attractive pink fully double flowers that are about 6.5 in diameter.

. Resistance to Powdery Mildew under commercial :nhouse conditions.

. Excellent postproduction longevity.

he accompanying colored photograph illustrates the :all appearance of the new cultivar, showing the colors as as it is reasonably possible to obtain colored repro-ions of this type. the photograph comprises a top per-:tive view of a typical flowering plant of 'Cavili'. Flower foliage colors in the photographs may differ from the al colors due to light reflectance.

ı the following description, color references are made to Royal Horticultural Society Colour Chart except where :ral terms of ordinary dictionary significance are used. following observations and measurements describe ts grown in Aalsmeer, The Netherlands, that were flow-

2 ered in November under commercial practice in a glass-covered greenhouse. Average day temperatures were 20° C. and average night temperatures were 18° C. Assimilation lights provided a maximum light level of 18,000 lux. Measurements and numerical values represent averages for six typical flowering plants.

Botanical classification: *Begonia×hiemalis* cultivar 'Cavili'.

Commercial classification: Elatior Begonia.

Parentage:

*Male or pollen parent.*—*Begonia socotrana.*

*Female or seed parent.*—*Begonia tuberosa.*

Propagation:

*Type.*—Terminal cuttings.

*Time to rooting.*—About 14 days with soil temperatures of 23° C.

*Rooting habit.*—Fine, fibrous and well-branched.

Plant description:

*Plant form.*—Upright and rounded potted plant, freely branching with good stem and stem base strength. Flowers are fully double and abundant. Plants flower continuously.

*Growth habit.*—Moderate growth rate and vigor. Suitable for 10 to 15-cm containers. Under optimal environmental and cultural conditions, usually 9 weeks are required to produce proportional 13-cm potted plants from terminal cuttings. Vegetative shoots are formed at basal nodes and flowering shoots are formed at upper nodes.

*Plant height.*—About 30 cm.

*Plant width.*—About 25 cm.

*Leaves.*—Arrangement: Simple, alternate. Size: Length: About 14cm. Width: About 12 cm. Shape: Asymmetrically cordate. Apex: Acute. base: Cordate. Margin: Doubly serrate. Texture: Smooth, shiny, leathery. Color: Young foliage, upper surface: 147A. Mature foliage: Upper surface: 139A. Lower surface: 182A. Venation: Upper surface: Light green. Lower surface: 147B.

Flower description:

*Flowering habit.*—Fully double flowers arranged in racemes. Many racemes in flower simultaneously. Flowering continuous.

*Natural flowering season.*—Plants will flower year around regardless of daylength, however plants will flower earlier and more abundantly if daylength is 12 hours or less. Usually plants start flowering after 7 weeks of start of short day/long night treatments.

*Flowers.*—Shape: Flattened oval. Diameter: About 6.5 cm.

*Tepals.*—Arrangement: Rosette. Shape: Flat, rounded with undulate margin. Quantity per flower: Usually about 19 per flower. Color: When opening: 38A/49A. Fully opened: Upper surface: 38A/49A. Lower surface: 38B/49A. Texture: Smooth, velvety, glabrous.

*Sepals*—Arrangement: Two, opposite. Shape: Oval. Color: 143C with red edge.

*Reproductive organs.*—Stamens: None. Pistils: None.

Postproduction longevity:

*Individual flowers.*—Generally 2 to 3 weeks.

*Whole plants.*—About 6 weeks under interior conditions.

Disease resistance: Plants of the cultivar 'Cavili' are resistant to powdery mildew under greenhouse conditions.

Seed production: Seed production has not been observed as reproductive organs are not formed.

It is claimed:

1. A new and distinct cultivar of Begonia plant named 'Cavili', as illustrated and described.

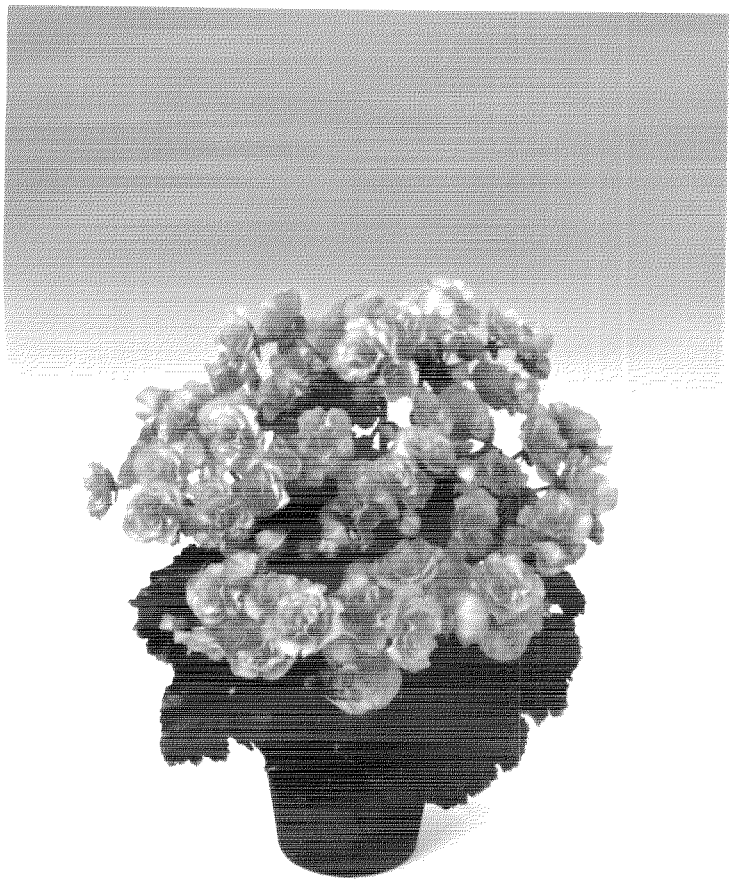

* * * * *